US011832934B1

(12) United States Patent
Zheng

(10) Patent No.: US 11,832,934 B1
(45) Date of Patent: Dec. 5, 2023

(54) JOINT MONITORING

(71) Applicant: Qingbin Zheng, Santa Clara, CA (US)

(72) Inventor: Qingbin Zheng, Santa Clara, CA (US)

(*) Notice: Subject to any disclaimer, the term of this patent is extended or adjusted under 35 U.S.C. 154(b) by 205 days.

(21) Appl. No.: 17/246,631

(22) Filed: May 1, 2021

Related U.S. Application Data

(60) Provisional application No. 63/019,432, filed on May 4, 2020.

(51) Int. Cl.
A61B 5/11 (2006.01)
A61B 5/00 (2006.01)
A61B 5/0531 (2021.01)
A61B 5/0205 (2006.01)
A61B 5/024 (2006.01)

(52) U.S. Cl.
CPC .......... *A61B 5/1126* (2013.01); *A61B 5/0002* (2013.01); *A61B 5/0205* (2013.01); *A61B 5/02416* (2013.01); *A61B 5/0531* (2013.01); *A61B 5/6812* (2013.01); *A61B 2562/0204* (2013.01); *A61B 2562/028* (2013.01); *A61B 2562/0219* (2013.01)

(58) Field of Classification Search
CPC ... A61B 5/1126; A61B 5/0002; A61B 5/0205; A61B 5/02416; A61B 5/0531; A61B 5/6812; A61B 2562/0204; A61B 2562/0219; A61B 2562/028
USPC ........................................................ 600/301
See application file for complete search history.

(56) References Cited

U.S. PATENT DOCUMENTS

| 4,737,710 | A | | 4/1988 | Van Antwerp et al. |
| 5,792,077 | A | | 8/1998 | Gomes |
| 5,826,578 | A | * | 10/1998 | Curchod ............ A63B 69/0059 600/595 |
| 5,980,472 | A | | 11/1999 | Seyl |
| 6,050,962 | A | | 4/2000 | Kramer et al. |
| 6,872,187 | B1 | | 3/2005 | Stark et al. |
| 8,165,844 | B2 | | 4/2012 | Luinge et al. |
| 8,246,462 | B1 | | 8/2012 | Tran et al. |
| 8,279,091 | B1 | | 10/2012 | Trab et al. |
| 8,421,448 | B1 | | 4/2013 | Tran et al. |

(Continued)

OTHER PUBLICATIONS

Zhao, "A Review of Wearable IMU (Inertial-Measurement-Unit)-based Pose Estimation and Drift Reduction Technologies", IOP COnf. Series: Journal of Physics: Conf. Series 1087 (2018).

(Continued)

*Primary Examiner* — Carl H Layno
*Assistant Examiner* — Michael J Lau
(74) *Attorney, Agent, or Firm* — Douglas L. Weller

(57) ABSTRACT

A joint movement monitoring device includes a joint pad that fits over a joint. The joint pad has a primary section placed over a first side of the joint and has an opposing section placed over a second side of the joint. A plurality of three-dimensional (3D) magnetic sensors are incorporated into the primary section of the joint pad. The 3D magnetic sensors are separated by a known distance. A magnet is incorporated into the opposing section of the joint pad. A controller obtains signals from the plurality of 3D magnetic sensors. The signals are used to detect magnet rotation angles related to 3D magnetic sensors within the plurality of 3D magnetic sensors. The detected magnet rotation angles are used to monitor joint position of the joint.

20 Claims, 15 Drawing Sheets

(56) References Cited

U.S. PATENT DOCUMENTS

| | | | |
|---|---|---|---|
| 9,019,349 B2 | 4/2015 | Richardson | |
| 9,119,569 B2 | 9/2015 | Chen et al. | |
| 9,551,562 B2 | 1/2017 | Janisch | |
| 9,642,572 B2 | 5/2017 | Mahfouz et al. | |
| 10,061,891 B2 | 8/2018 | Grundlehner et al. | |
| 10,278,647 B2 | 5/2019 | Salehizadeh et al. | |
| 2006/0113990 A1 | 6/2006 | Schodlbauer | |
| 2013/0217998 A1* | 8/2013 | Mahfouz | A61B 5/4533 600/595 |
| 2016/0242646 A1* | 8/2016 | Obma | A61B 5/01 |
| 2016/0246369 A1 | 8/2016 | Osman | |
| 2016/0338621 A1* | 11/2016 | Kanchan | A61B 5/11 |
| 2016/0338644 A1* | 11/2016 | Connor | A61B 5/1126 |
| 2017/0090668 A1 | 3/2017 | Chen et al. | |
| 2017/0181689 A1* | 6/2017 | Lin | A61B 5/1107 |
| 2017/0231533 A1* | 8/2017 | Qu | A61B 5/112 600/409 |
| 2017/0277138 A1* | 9/2017 | Kaji | A61B 5/112 |
| 2019/0283247 A1* | 9/2019 | Chang | A61B 5/1121 |
| 2020/0033958 A1 | 1/2020 | Bieglmayer | |
| 2020/0054288 A1* | 2/2020 | Vural | G06N 3/08 |

OTHER PUBLICATIONS

Orlando Adas Saliba Junior et al. "Pre- and Postoperative Evaluation by Photoplethysmography in Patients Receivign Surgery for Lower-Limb Varicose Veins", Internal Journal of Vascular Medicine vol. 2014, Articl ID 562782. Feb. 2014.

Ryan Clark, et al., "Tracking joint angles during whole-arm movements using electromagnetic sensors", Brigham Young University Faculty Publications 4174, BYU ScholarsArchive, https://scholarsarchive.byu.edu/facpub/4174, 2020.

\* cited by examiner

JOINT MONITORING

BACKGROUND

Motion analysis to study joint-related biomechanics can be performed by measuring body kinematics via motion capture systems such as optical, inertial measurement units (IMU), electro-goniometers, and mechanical tracking. Each technology has advantages and limitations pertaining to their effectiveness and convenience of use. For example, optical systems are often used for full body motion capture, but the required complex setups and data processing systems can make these systems less attractive for daily life health assessment and monitoring a single joint or body part. Electro-goniometer and mechanical tracking systems are adapted to monitor single joint motion but have poor portability restricting their flexibility for use in various situations such as during an athletic competition. IMU-based systems are wearable and portable but have limited fields of operation, significant integration drift issue and high error rates that require more frequent sensor calibration to compensate.

DETAILED DESCRIPTION

A joint movement monitoring system can be used for health monitoring and interactive skeletal tracking of an indoor or an outdoor exercise program. The joint movement monitoring system allows monitoring of the motions of body parts with respect to a joint. Such human body joint monitoring can help a person by regularly monitoring the mobility status and assisting to maintain regular physical activities/exercises. The joint movement monitoring systems described, which allow for continuous monitoring of joint activity and health, can record and extract important parameters for early diagnosis, leading to early treatment of mobility-related problems. This facilitates analysis of human joint posture and movement that can be used for an extensive range of mobility-related activities such as rehabilitation, sports medicine, human activity assessment and virtual guided training. The joint movement monitoring system enables the gathering of accurate data reliably in real life using a comfortable appliance and without frequent sensor calibration.

A joint health monitoring system can include a calibration-free skeletal tracking module that utilizes three-dimensional (3D) magnetic sensors and kinematic model to track motion, a muscle force and joint wear-out monitoring module that utilizes a microelectromechanical systems (MEMS) sensor to track joint condition, and a biosensor module that utilizes photoplethysmography (PPG) and/or electrodermal activity (EDA) to track biomarkers. A joint health monitoring system can be configured to fuse data and generate a skeletal/character model, which can be monitored and animated in real time on a display. For example, the skeletal models are used to interact in a world scene (gym, running trail, Yoga place, golf course, swimming pool), or a shared animated space with an artificial intelligent health examiner/personal trainer or animated movie character.

For example, a joint health monitoring system can be worn by multiple users in a competition, a group exercise or training class setup. In such examples, each user from a remote location may use two, four or another number of joint movement monitoring devices. Joint health monitoring systems can be used to produce data that is monitored, stored and studied, for example, using a cloud-based health monitoring system. A joint health monitoring system can be configured to detect and report emergency situations.

Figure 1:
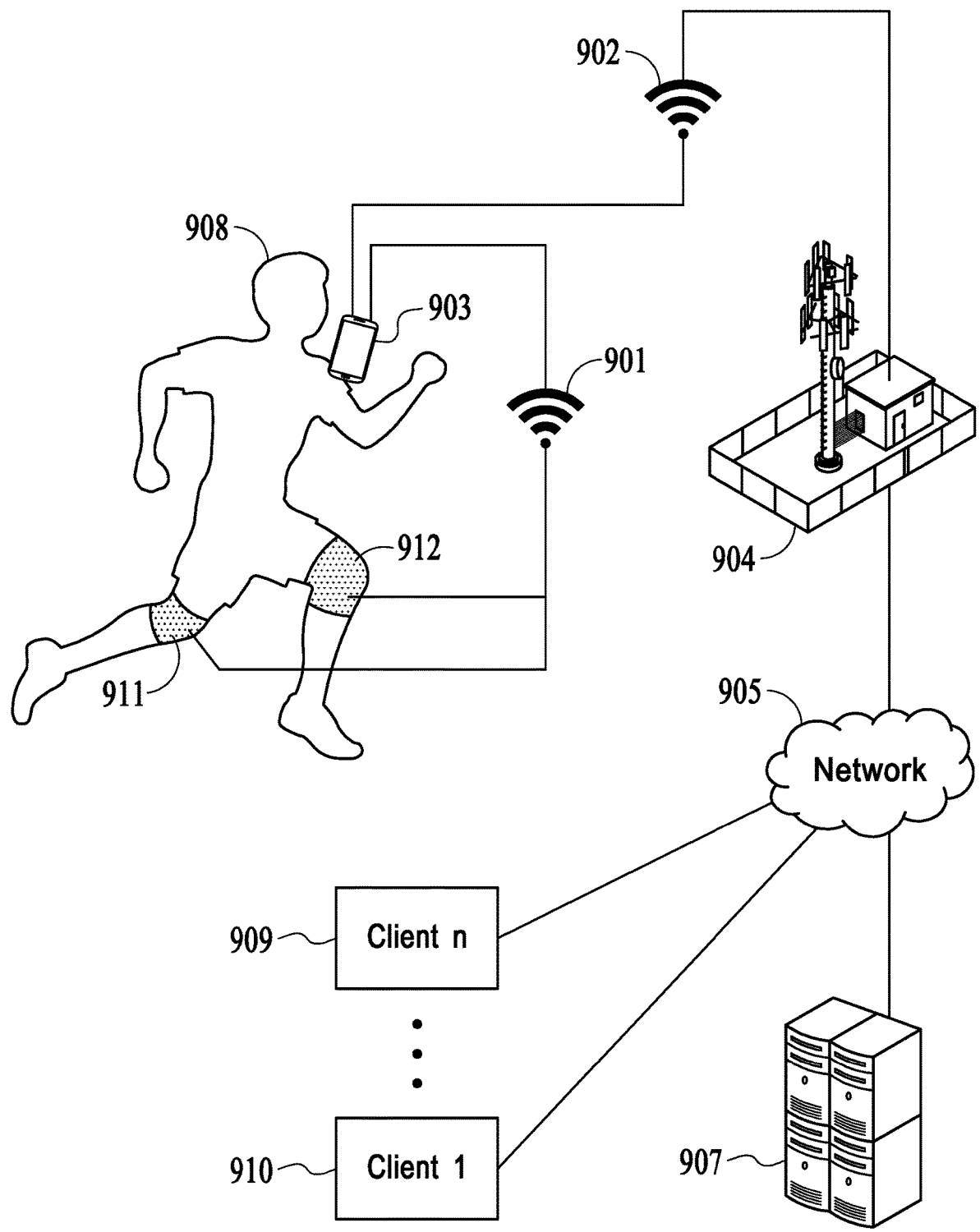
FIG. 1 illustrates a joint movement monitoring system for health monitoring and interactive skeletal tracking of an indoor or an outdoor exercise program.

FIG. 1 illustrates an example of a joint movement monitoring system that can be used for health monitoring and interactive skeletal tracking of an indoor or an outdoor exercise program. A user 908 is shown wearing a joint movement monitoring device 911 and a joint movement monitoring device 912. Joint movement monitoring device 911 and joint movement monitoring device 912 communicate with a portable device 903 through a wireless link 901. For example, wireless connection 901 can be implemented using Bluetooth technology, Wi-Fi or some other wireless protocol. Alternatively, a wired link can be used to connect joint movement monitoring device 911 and joint movement monitoring device 912 to portable device 903. For example, portable device 903 can be any general or special purpose smart device known in the art, including but not limited to a mobile device, a cellular phone, a tablet, and so on.

For example, portable device 903 can be configured to execute a health monitoring application for fusing data and generating a skeletal model that can be monitored and tracked in real time on a display of portable device 903 or a display of some other device such as another portable device, a computer display, a display panel, a display used by remotely connected users and so on. For example, the monitoring can be in real time so that as a user changes leg positions, for example, when, running, biking, swimming or walking, the health indications and changes in skeletal joints are changed in real time on the display.

For example, portable device 903 can be connected to a cellular base station 904 via a cellular network 902 and can function as a client in communication over a network 905 with a cloud-based health monitoring center 907.

For example, portable device 903 transmits GPS data, as well as inputs from joint movement monitoring device 911 and joint movement monitoring device 912, to health monitoring center 907. For example, health monitoring center 907 processes the inputs using artificial intelligence such as knowledge representation and reasoning (KRR) to monitor fatal signs, biomarkers and so on. The resulting information can be transmitted to portable device 903, and others such as a client 909 and a client 910 that are connected to network 905. For example, client 909 and client 910 can each be a service center or another type of user connected to network 905. For example, portable device 903 can display a message and provide vibration feedback to user 908. A service center or other user on network 905 can be notified to provide assistance if needed.

For example, health monitoring center 907 stores the historical health data, health analysis result and medical record of user 908.

For example, based on portable device 903's GPS data, health monitoring center 907 can create an animated world scene such as a gym, a running trail, an exercise class, a golf course or a swimming pool in which users wearing joint movement monitoring devices can interact with each other, communicating, sharing information skeletal models and so on. For example, voice volume of each portable device can be weighted by source based on user distance in the animated scene, so that the voice volume of those closest to a user in the animated world scene will be louder than those more distant from the user in the animated world scene. This allows users that are remotely distant to interact as if they were physically presented in the animated world scene.

Figure 2:
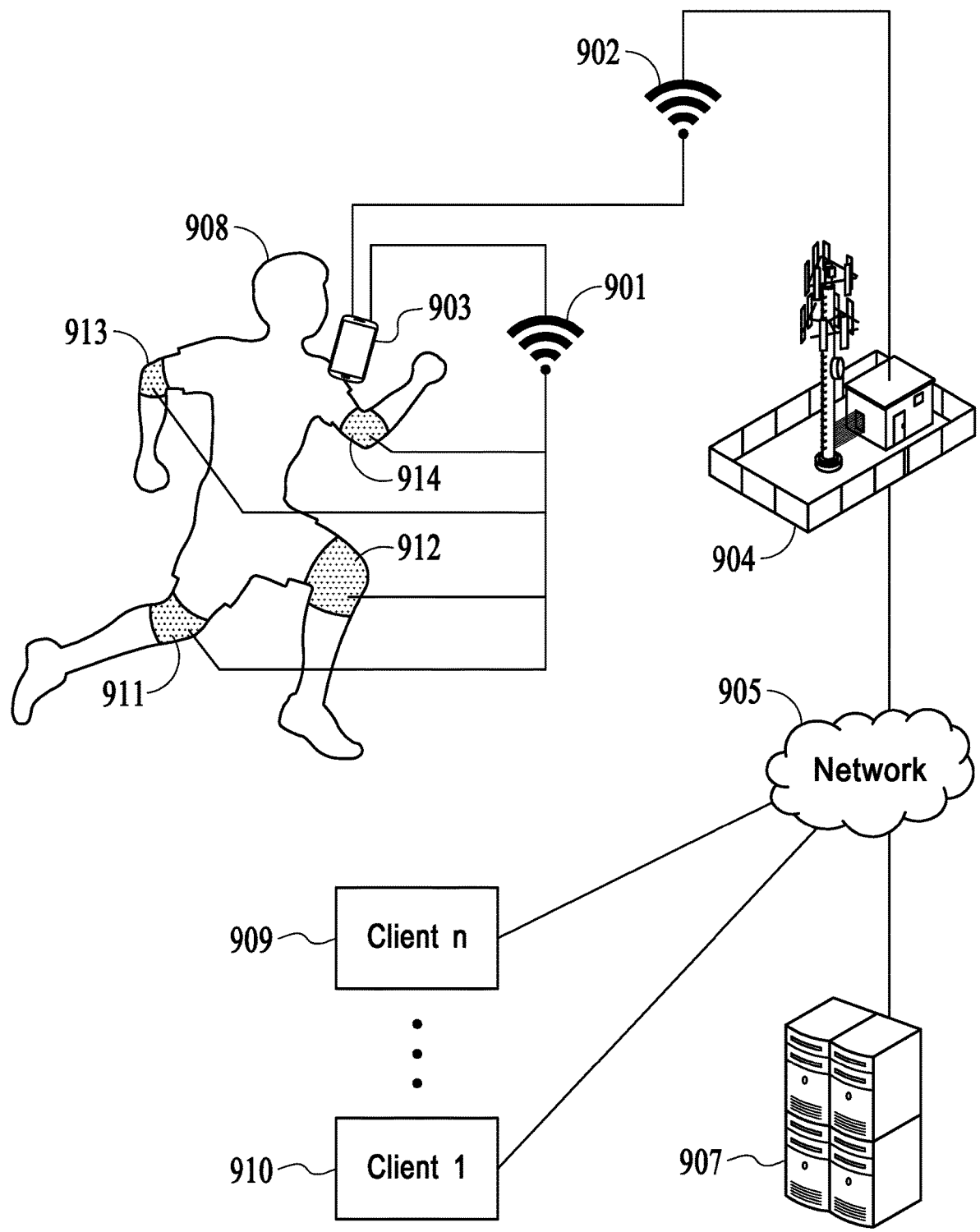
FIG. 2 illustrates a joint movement monitoring system for full body skeletal tracking.

FIG. 2 shows user 908 wearing an additional joint movement monitoring device 913 and an additional joint movement monitoring device 914. Joint movement monitoring device 913 and additional joint movement monitoring device 914 can be implemented similar to joint movement monitoring device 911 with the exception that joint pads are sized to fit an elbow rather than a knee. When the same sensor configuration is used for both the knees and elbow, the location and IP address of joint movement monitoring devices 911 through 914 can all be identified automatically by the joint moving pattern and using Bluetooth positioning service. This can reduce or eliminate the set-up time for joint movement monitoring devices.

For example, as shown in FIG. 2, joint movement monitoring device 913 and joint movement monitoring device 914 are used to monitor position of the elbows of user 908 while joint movement monitoring device 911 and joint movement monitoring device 912 are used to monitor position of the knees of user 908. Other joint movement monitoring devices may be worn to track other joints, such as ankles, fingers, toes and so on. The resulting skeletal tracking can be presented in the shared space on a display of a remotely connected client, who may be viewing content or sharing in an interactive experience.

Figure 3:
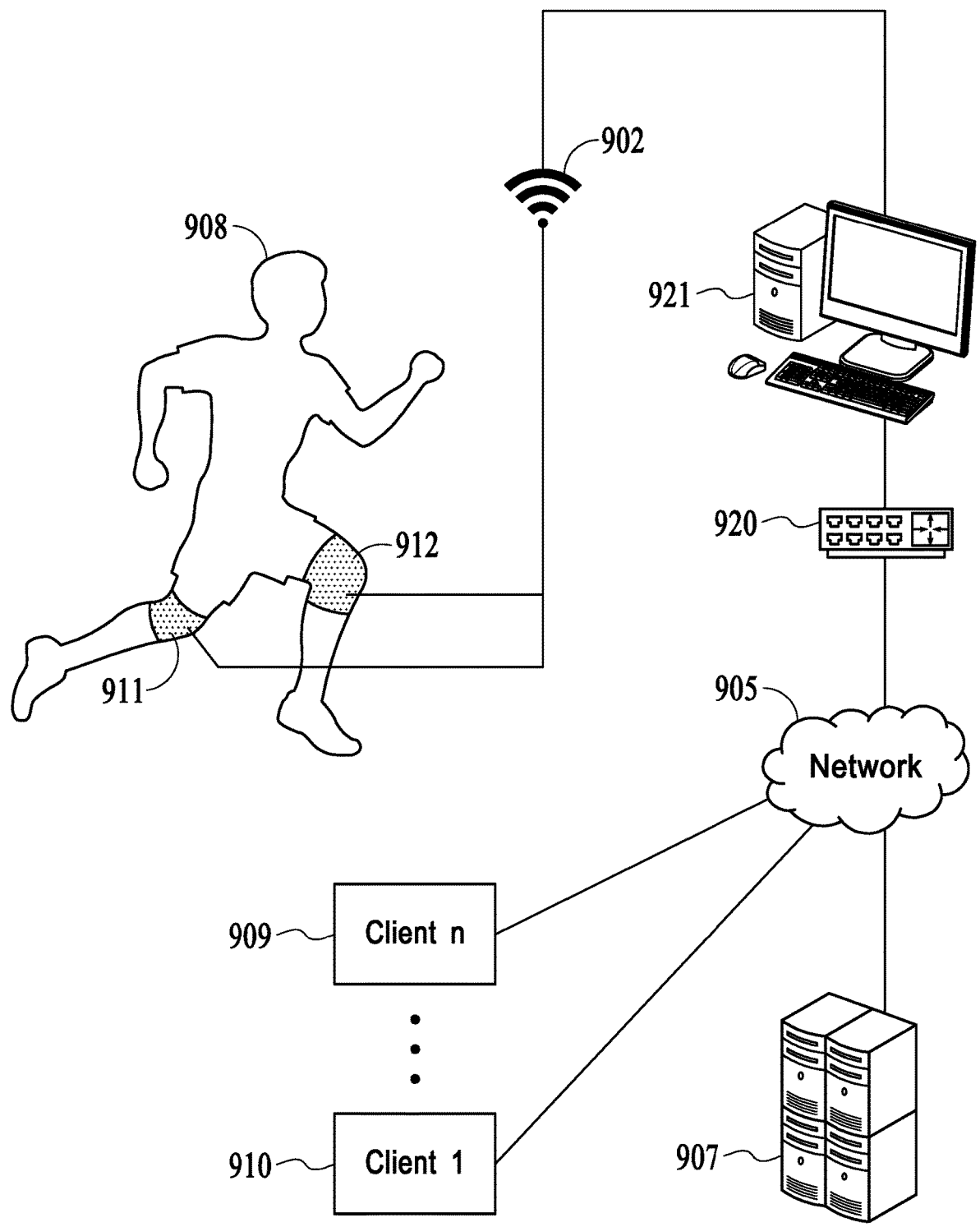
FIG. 3 illustrates a joint movement monitoring system for health monitoring and interactive skeletal tracking of an indoor workout program.

FIG. 3 illustrates the joint movement monitoring system configured for health monitoring and interactive skeletal tracking of an indoor workout program. Here, cellular base station 904 shown in FIG. 1 is replaced with a computer 921 connected to network 905 via a modem 920 or another network communication device such as a router. Computer 921 transmits inputs from joint movement monitoring device 911 and joint movement monitoring device 912, to health monitoring center 907. For example, health monitoring center 907 creates a shared animated space, in which the skeletal model of user 908 is used to interact with artificial intelligent health examiner/personal trainer or animated movie characters. For examples, joint movement monitoring device 911 and 912 may be worn by multiple user 908 in a competition, group exercise or training class setup. In such examples, each user from a remote location may additionally wear joint movement monitoring devices for elbows as well as joint movement monitoring devices for knees. Joint movement monitoring devices can also be worn for other joints. For example, in a shared animated space, one of the animated characters can be an instructor co-located or interfacing in an online class scenario. The historical health data, health analysis result and medical record of user 908 can be monitored, stored and used for studies by the health monitoring system 907.

For example, user information (name, company etc.) may be related to the location obtained by direction and step counts from access point and/or Wi-Fi positioning system (WPS). User information, including location, may be shared with other users in the scene. For example, health monitoring center 907 processes the inputs using artificial intelligence. The output from the knowledge representation and reasoning (KRR), such as fatal signs and biomarkers etc., is transmitted to computer 921, other users in shared space 910 and service centers 909, which are also clients in the network. Computer 921 can display a message and provide audible feedback to user 908. Service centers 909 and other users in shared space 910 can provide assistance.

Figure 4:
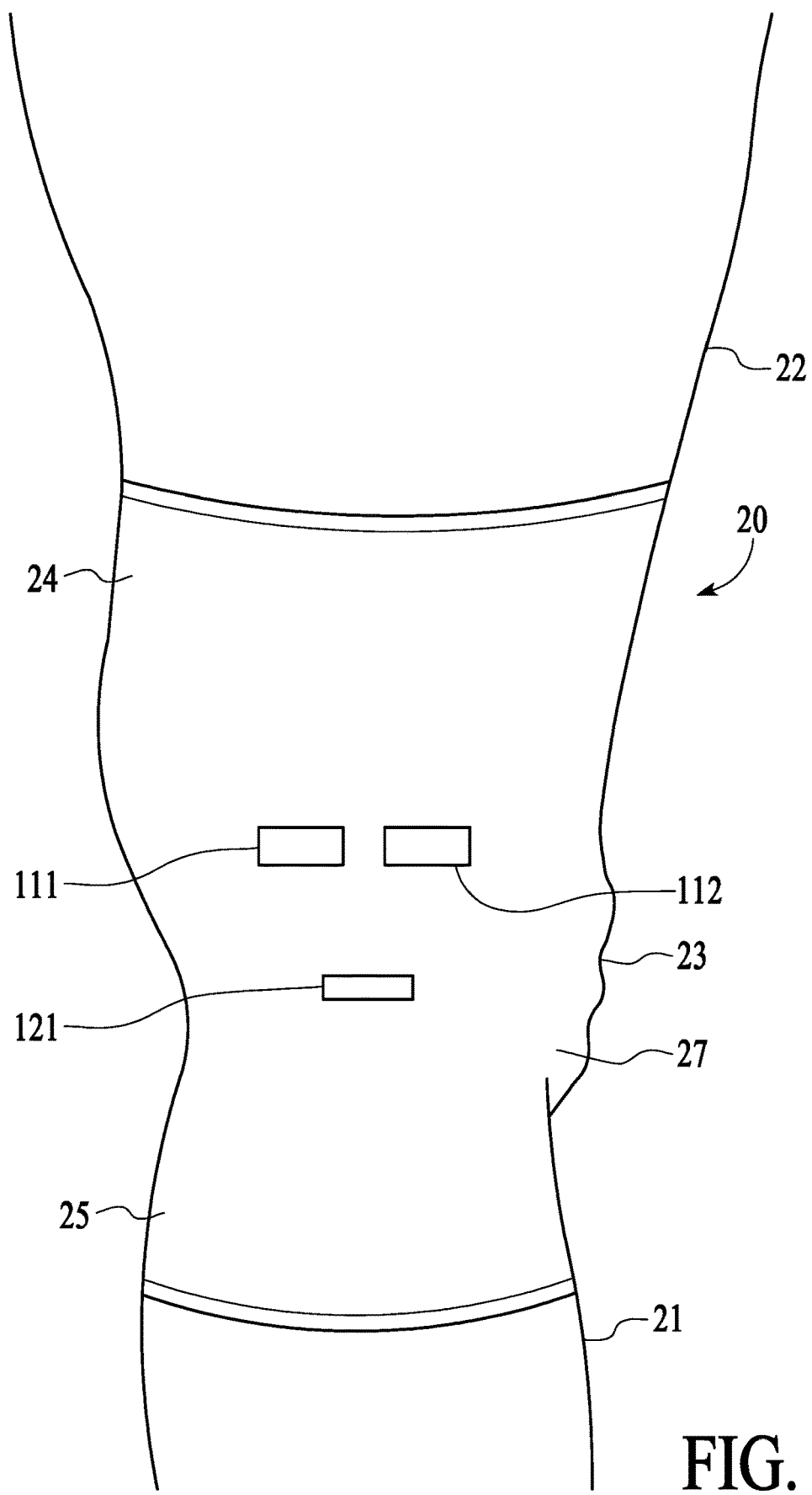
FIG. 4 illustrates a joint movement monitoring device having a plurality of 3D magnetic sensors and magnet defined thereon.

FIG. 4 shows joint movement monitoring device 911 includes a joint pad 27 sized to fit a knee. A user leg 20 is shown including a shank 21 and a thigh 22 joined by a knee joint 23. Joint pad 27 is worn over leg 20 at knee joint 23 as shown.

Figure 13:
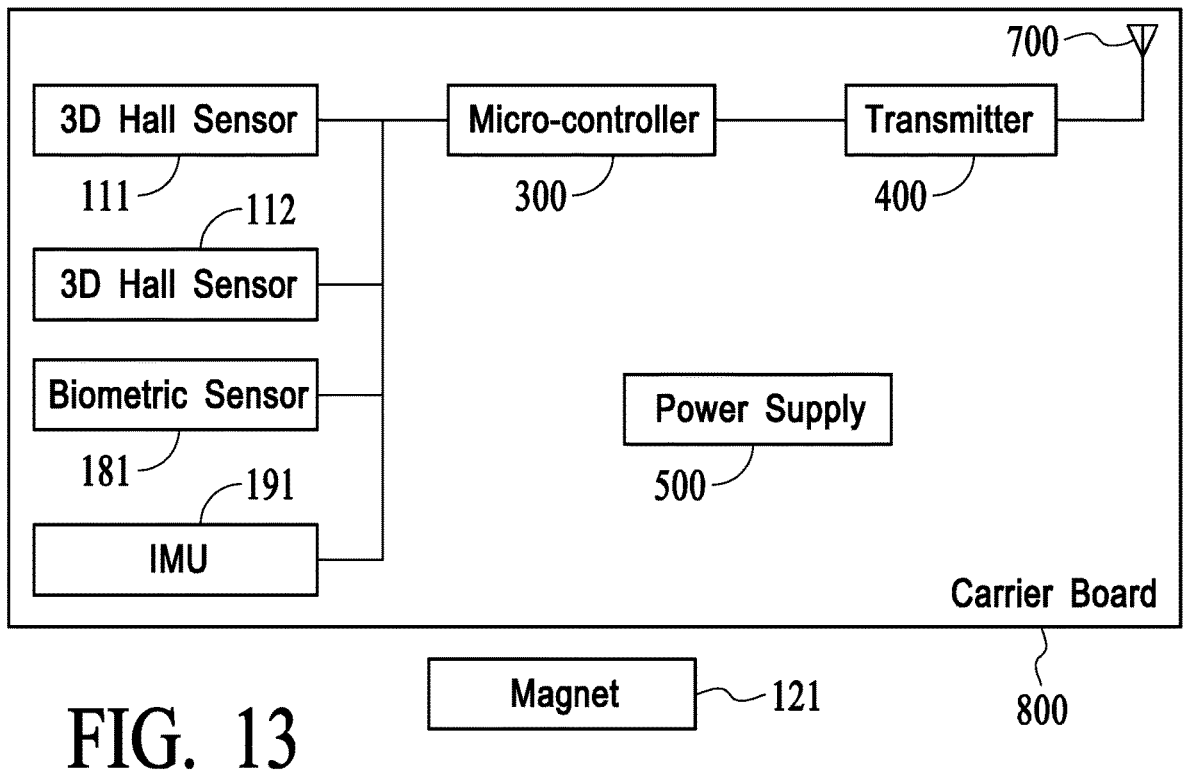
FIG. 13 illustrates a block diagram of a sensor system.

Joint movement monitoring device 911 can be used to monitor and track motion of knee joint 23. For example, a 3D magnetic sensor 111 and a 3D magnetic sensor 112 are incorporated into a primary section 24 of joint pad 27. For example, 3D magnetic sensor 111 and a 3D magnetic sensor 11 may be placed directly on joint pad 27 or may be on a rigid section of a carrier board 800, as shown in FIG. 13, that is attached to or otherwise incorporated into joint pad 27. For example, 3D magnetic sensor 111 and 3D magnetic sensor 112 are 3D Hall effect sensors.

Joint pad 27 also has an opposing section 25 on which is incorporated a magnet 121. Primary section 24 and opposing section 25 of joint pad 27 are on opposite sides of knee joint 23.

Figure 10:
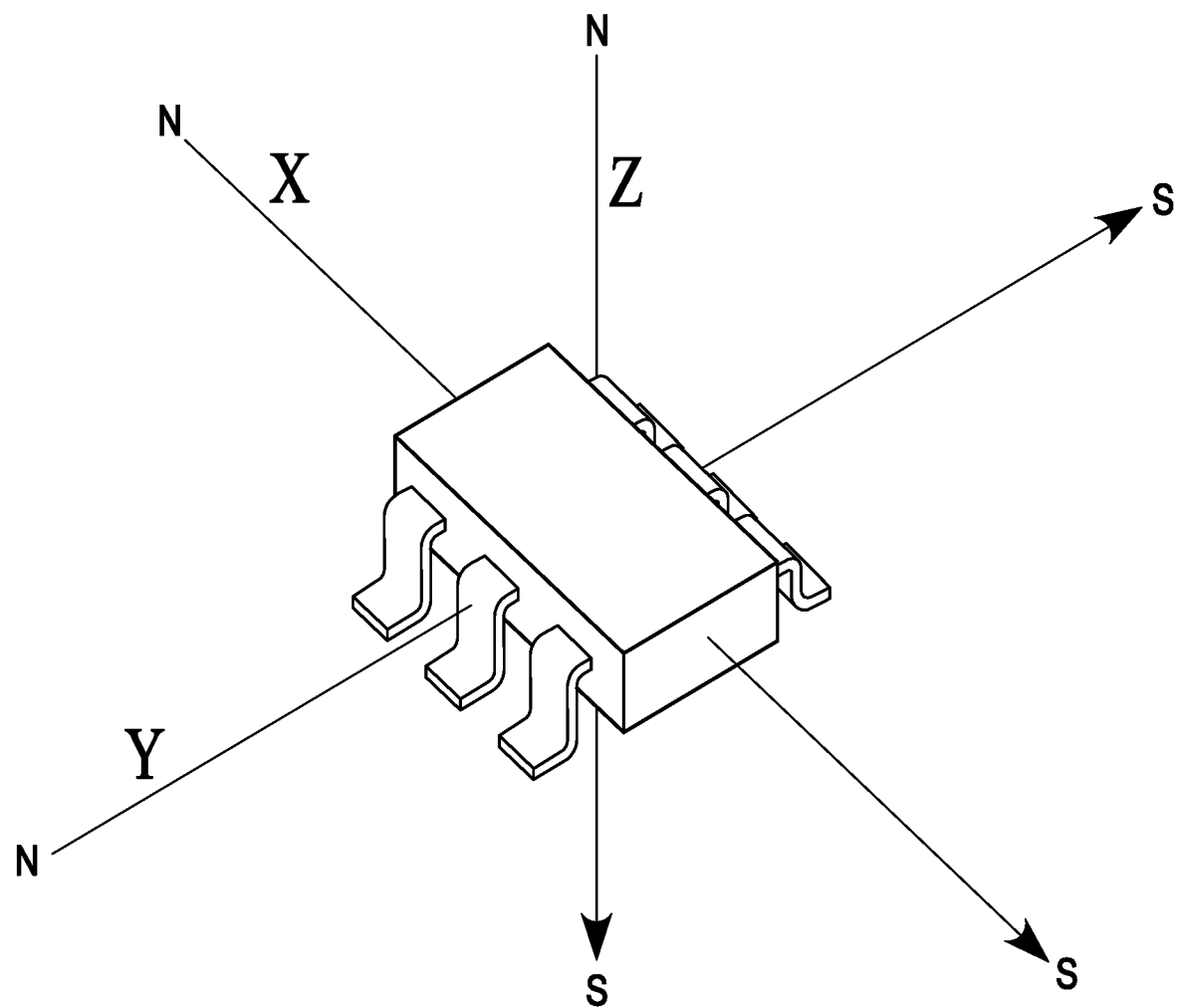

The circuitry in carrier board 800, shown in FIG. 13 is configured to read 3D magnetic sensor 111 and 3D magnetic sensor 112 and to transmit data derived from the reading of 3D magnetic sensor 111 and 3D magnetic sensor 112 to computing device 903, shown in FIG. 1, for processing to generate data representing angle and pose of knee joint 23. For example, 3D magnetic sensor 111 and 3D magnetic sensor 112 have known separation on joint pad 27, allowing calibration-free measurement of knee joint 23 movement in a kinematic model, as illustrated in FIG. 10.

Figure 5:
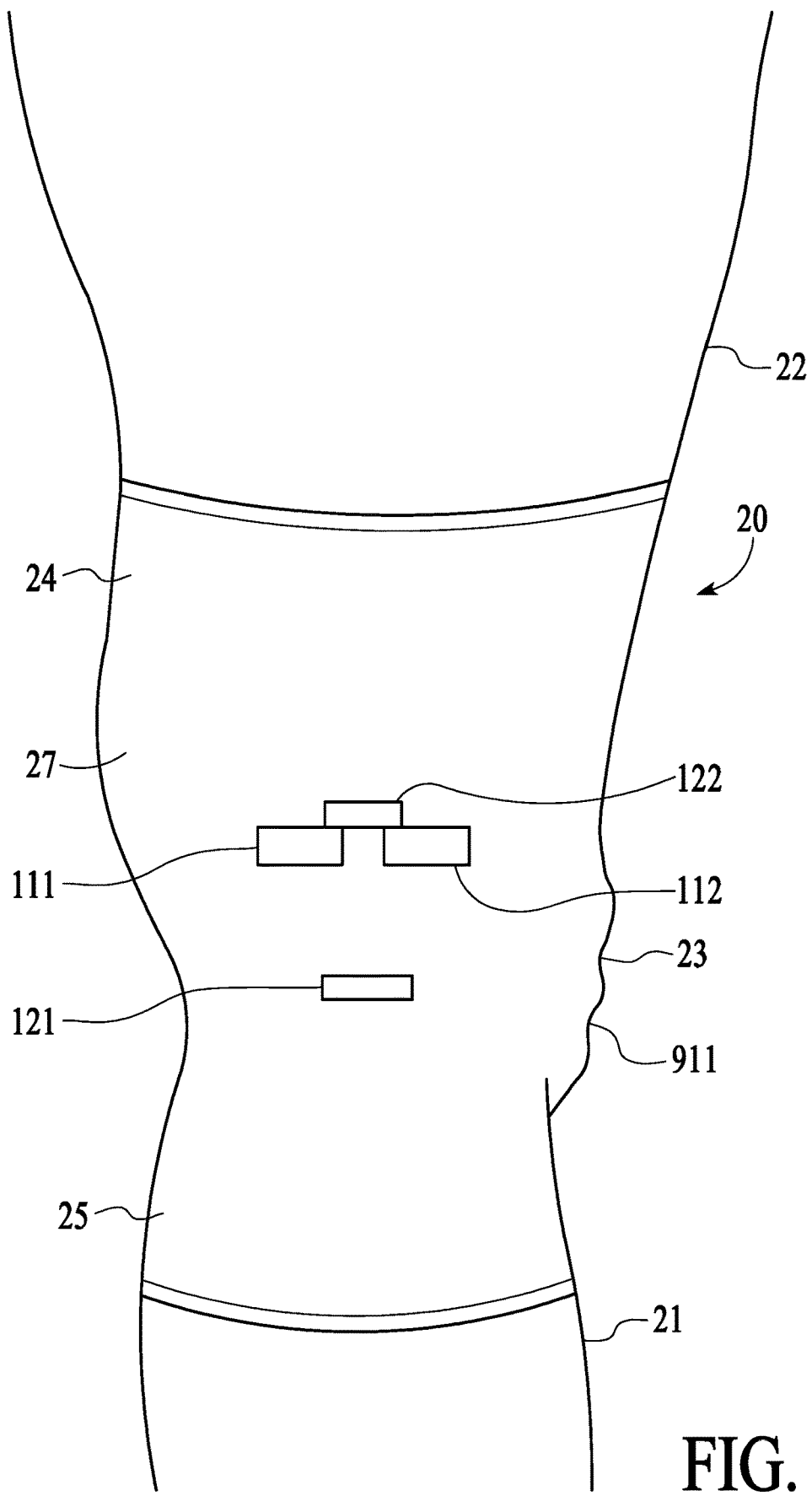
FIG. 5 illustrates a joint movement monitoring device having multiple magnets defined thereon.

Instead of just one magnet 121, as shown in FIG. 4, multiple magnets can be included in joint movement monitoring device 911, as shown in FIG. 5. Specifically, magnet 122 has been added. For example, magnet 121 and magnet 122 are configured to direct the magnet flux on 3D magnetic sensor 111 and 3D magnetic sensor 112 in 3D domain to improve joint angle measurement linearity.

Additional sensors may also be added. These additional sensors can include, for example, pressure sensors, inertial measurement unit (IMU) sensors, electromyography (EMG)

sensors, galvanic skin response (GSR) sensors, acoustic emission (AE) sensors, micro electro-mechanical systems (MEMS) sensors, photoplethysmography (PPG) sensors, electrodermal activity (EDA) and other types of sensors including other types of biosensors.

Figure 6:
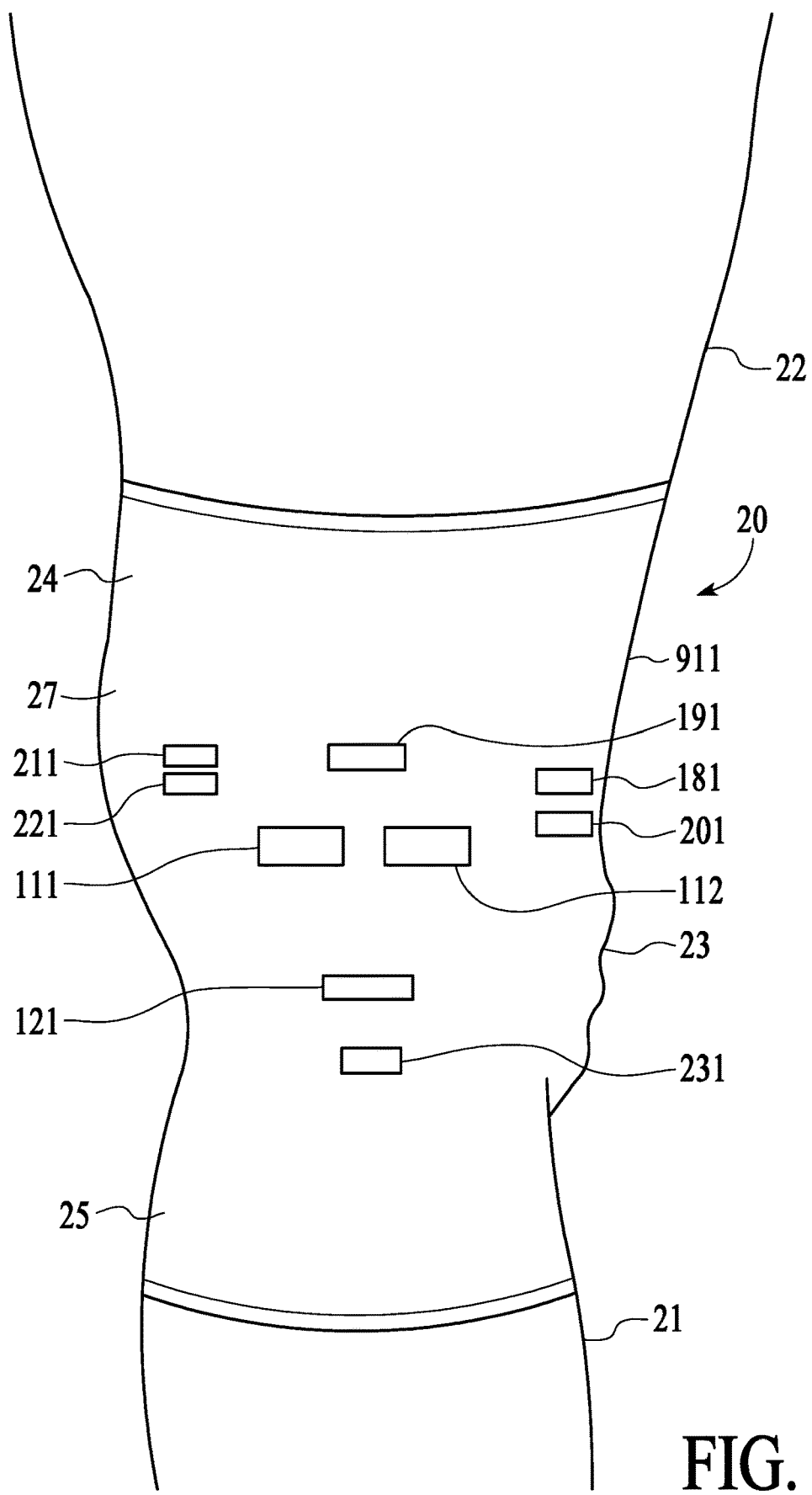
FIG. 6 illustrates a joint movement monitoring device having a plurality of 3D magnetic sensors and other types of sensors.

For example, FIG. 6 shows additional sensors included in joint movement monitoring device 911. For example, joint movement monitoring device 911 is shown to include an IMU 191 in the rigid section of carrier board 800, shown in FIG. 13, to measure knee joint 23 movement. A muscle force and joint wear-out monitoring module in the flex section of carrier board 800, shown in FIG. 13, can also be added that utilizes a MEMS sensor 211 and an AE sensor 221 to track joint 23 condition. Additionally, a biosensor module can be included in the flex section on the other side of carrier board 800, shown in FIG. 13, that utilizes a PPG sensor 201 and an EDA sensor 181 to track biomarkers. The circuitry in carrier board 800, shown in FIG. 13, may be configured to read 3D magnetic sensor 111 and 3D magnetic sensor 112 as well as MEMS sensor 211, AE sensor 221, PPG 201 and EDA 181, and transmit data derived from the reading of the above sensors to computing device 903, shown in FIG. 1.

For example, joint movement monitoring device 911 can be configured to fuse data, generate a pose of a skeletal joint 23 and derive joint 23 health indicators (muscle strength, pulse rate etc.). For example, PPG sensor 201 can provide continuous information regarding a user's pulse rate, respiratory rate, and oxygen saturation. However, PPG sensors are susceptive to motion, often causing false signal due to motion artifact. When exposed to knee 23 bending, PPG Sensor 201 will move, and the cross-sectional area of the blood vessel may change. Thus, PPG sensor 201 reading may be disturbed in movement. The distortion of the PPG waveform is strongly correlated with the knee bending. For example, a recursive least squares active noise cancellation technique using 3D magnetic sensor 111 and 3D magnetic sensor 112 reading as an input for a Finite Impulse Response (FIR) or Laguerre model can be used to compensate for noise resulting from joint movement. In the FIR model, the actual PPG sensor output p is corrupted and e is the distortion signal component added to the true signal. $p_o$ is the heart portion of the PPG signal and is given by $p_o$=p−e. The estimation of e can be predicted by:

$$e(t)=\rho(t)^T\beta(t)$$

Where $$\rho(t)=[\theta(t-1) \ldots \theta(t-i) \ldots \theta(t-n)]^T$$

$$\beta(t)=[a_1 \ldots a_i \ldots a_n]$$

In the above equation, θ(t) is the joint angle measured by the 3D magnetic sensor at each time step and $a_i \ldots a_n$ are coefficients to be determined with various real-time computation algorithms, including the standard Recursive Least Squares (RLS).

Alternatively, histogram and factorial design can be used to derive Venous Recovery Time (VRT) in daily life for detecting and preventing varicose veins in earlier stage. Knee angle change will drive the venous blood in the veins in the proximal direction towards the heart or refill the veins in the legs with blood, and this causes PPG signal wave. VRT, the duration from bending and until the signal return to baseline at rest is a strong indication of possible incompetency of the venous valves.

Figure 7A:
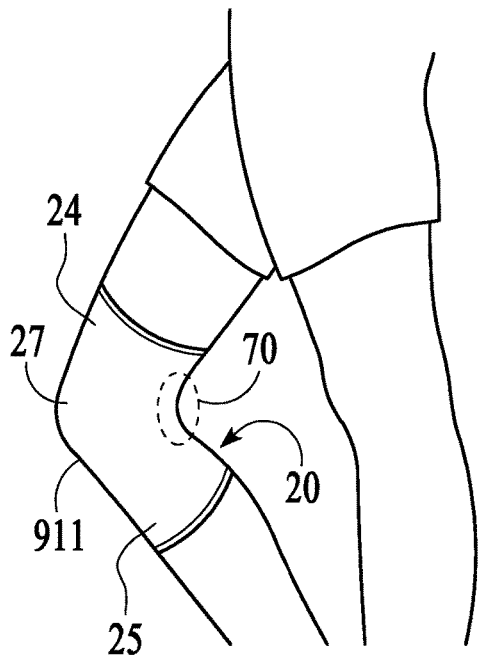
FIG. 7A and FIG. 7B illustrate a joint movement monitoring device being used to monitor joint health.
Figure 7B:
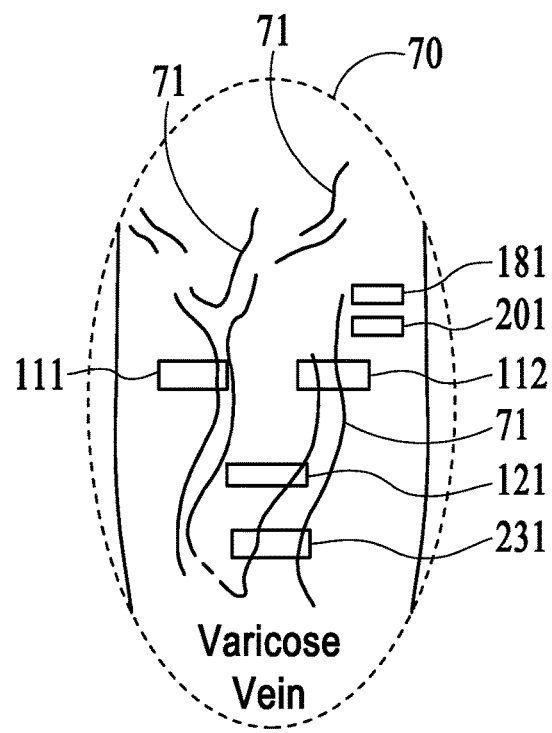

For example, an expanded section 70 of FIG. 7A is shown in FIG. 7B. FIG. 7B illustrates varicose veins 71 being monitored in daily life using PPG 201 and MEMS pressure sensor 231 signal with respect to joint angle as measured using 3D magnetic sensor 111 and 3D magnetic sensor 112 and time in the form of a histogram. The PPG signal and venous blood pressure at primary section 24 of joint pad 27 are measured when the joint is bending. Also, the duration from bending and until the PPG signal return to baseline is monitored while the knee is returned to minimum flexion angle at rest. The acquired data is compared to lab data using factorial experiment to derive equivalent VRT, which allows the effects of physical inactivity and venous tourniquet to be studied and to thereby avoid or minimize joint pain in old age and improve living standard of users.

Figure 8:
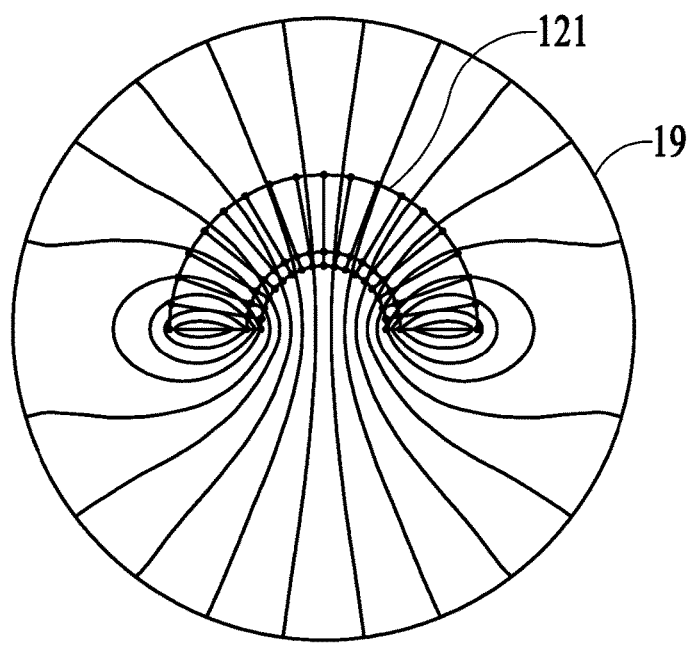
FIG. 8 illustrates a radial symmetric magnet.

FIG. 8 illustrates the magnetic field of a radial symmetric magnet. As shown, magnet 121 generates a radial symmetric magnetic field 19. Magnet 121 is configured to generate a corresponding radial symmetric magnetic field 19 oriented directly on the 3D magnetic sensors. For example, for an arbitrary 3D magnetic sensor location in the thigh 22 section of knee joint 23, the magnetic field vector H always lays from the magnet to the 3D magnetic sensors and can be mathematically represented in terms of the relationship between 3D magnetic sensor spatial angle and magnetic field 3D angle (as shown in FIG. 10):

$$\cos\beta 1 = B_{x1}/\sqrt{B_{x1}^2 + B_{y1}^2 + B_{z1}^2}$$

$$\sin\gamma 1 = B_{z1}/\sqrt{B_{x1}^2 + B_{y1}^2 + B_{z1}^2}$$

In the above equation Bx1, By1 and Bz1 are magnetic sensor readings.

Figure 9:
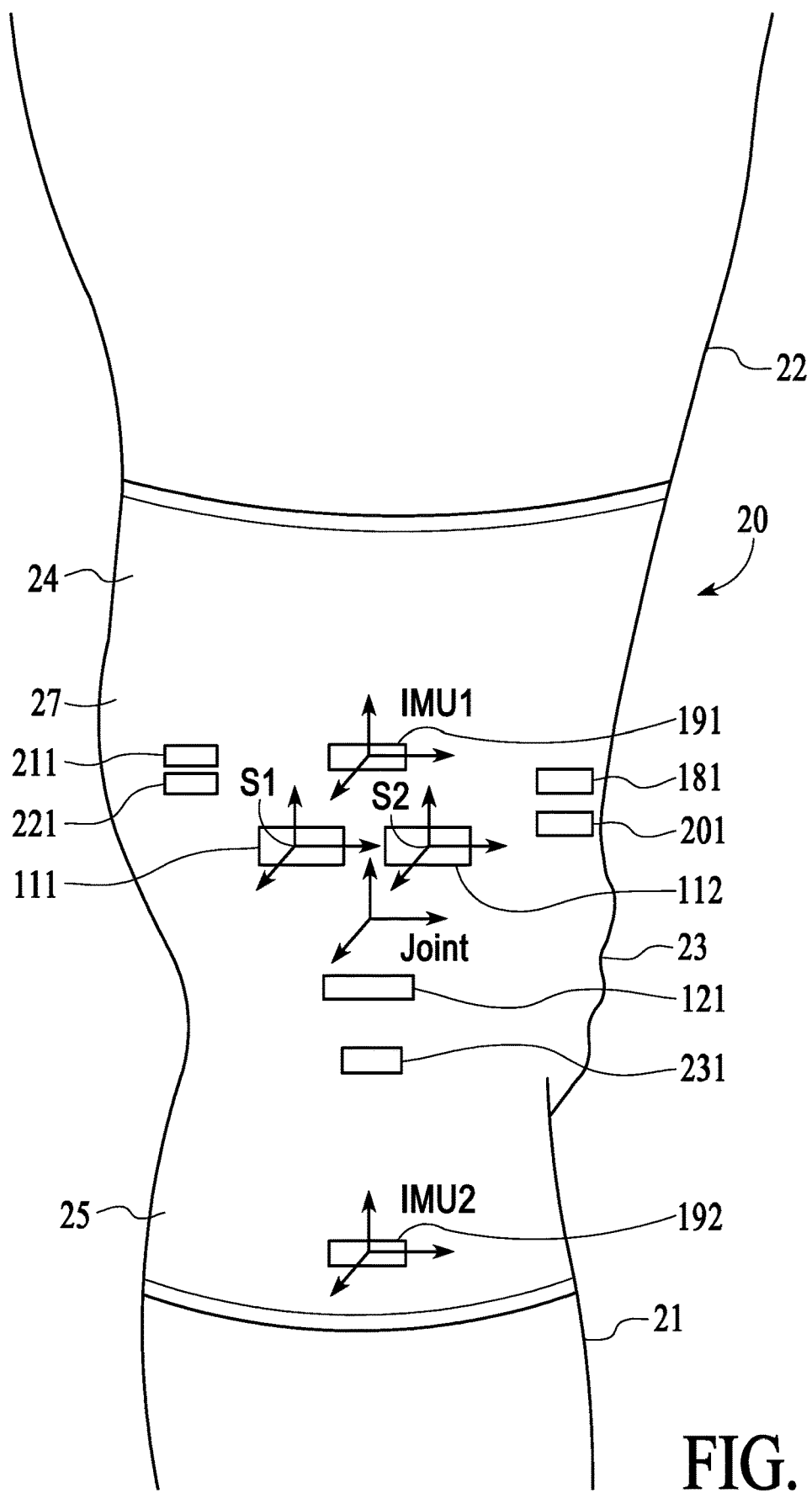
FIG. 9 and FIG. 10 show diagrammatic views of a frame of reference and coordinate system, respectively.

FIG. 9 and FIG. 10 illustrate diagrammatic views of a frame of reference and coordinate system as used in kinematic modeling. As shown in FIG. 9, for joint movement monitoring device 911 used in monitoring and tracking motion of knee joint 23, the joint turning axis is defined as the global x coordinate, and magnet 121 turns with the joint in the global y, z plane. As the joint turning axis meets the joint turning plane at the global origin, the global y coordinate is defined as from the global origin to magnet 121, and the global z coordinate is perpendicular to the global x, y plane from the global origin.

For example, the global reference frame may be further referenced by gravity. For example, FIG. 9 shows an additional IMU 192 added to opposing section 25. IMU 191 and IMP 192 are configured so that IMU 191 is secured to thigh 22 by being placed on carrier board 800. IMU 192 is secured on the shank 21 via opposing section 25 of joint pad. IMU 191 and IMU 192 each have a three-axis inertial coordinate system. In this way, IMU 191 and IMU 192 are configured to monitor the motion of user leg 20. To this end, the output signals generated by the inertial IMU 191 and IMU 192 may be referenced to the global coordinate system mentioned above to determine the absolute location of thigh 22 and shank 21 of user leg 20 in static state or slow-motion state of the joint.

For example, vector algebra provides a means to calculate joint absolute angle ϕ in midstance phase of a running/walking gait cycle using the apparent gravity vector between IMU 191 and 192 accelerometer readings. The scalar product a·b between any two IMU accelerometer vectors a and b gives the joint angle ϕ. This result is easily proved by applying the triangle cosine theorem to the triangle with sides comprised of the vectors a, b and a-b.

$$a \cdot b = \begin{pmatrix} a_x \\ a_y \\ a_z \end{pmatrix} \cdot \begin{pmatrix} b_x \\ b_y \\ b_z \end{pmatrix} = a_x b_x + a_y b_y + a_z b_z = |a||b|\cos\varphi$$

$$\cos\varphi = \frac{a_x b_x + a_y b_y + a_z b_z}{\sqrt{a_x^2 + a_y^2 + a_z^2} + \sqrt{b_x^2 + b_y^2 + b_z^2}}$$

In the equation above, $a_x$, $a_y$, $a_z$ are IMU 191 acceleration readings, and $b_x$, $b_y$, $b_z$ are IMU 192 acceleration readings.

The above calculated joint absolute angle $\phi$ may then be used as the starting angle for motion tracking in the remained phases of running/walking gait cycle. 3D hall sensor data starts to fuse in to determine relative motion between thigh 22 and shank 21 in fast joint movement, in order to minimize IMU drifting and improve accuracy. Both absolute and relative movement of the joint can be monitored with this configuration.

Calibration-free health measurement is highly desired for daily health assessment. 3D magnetic sensor 111 and 3D magnetic sensor 112 providing magnetic field detection in x, y, and z directions, and being linked together with a defined separation between them can provide calibration-free joint movement tracking. For example, FIG. 10 shows a typical 3D Hall effect sensor currently available from manufacturers such as Infineon, Melexis or Allegromicro. As shown in the FIG. 10, each individual 3D magnetic sensor has its own three-dimensional sensing coordinate, defined by the 3D magnetic sensor manufacturer. Sensor data fusion occurs in portable device 903, where the vector calculation also is performed to determine the joint turning angle using kinematic model. These sensing coordinates x, y, z linked and computed by portable device 903 yield relationships as magnet 121 moving in global space as vector points, and resultant lines of magnetic flux directly from magnet 121 onto 3D magnetic sensor 111 and 3D magnetic sensor 112 caused by the radial symmetric magnetic field 19, as shown in FIG. 10, simplify these relationships.

Figure 11:
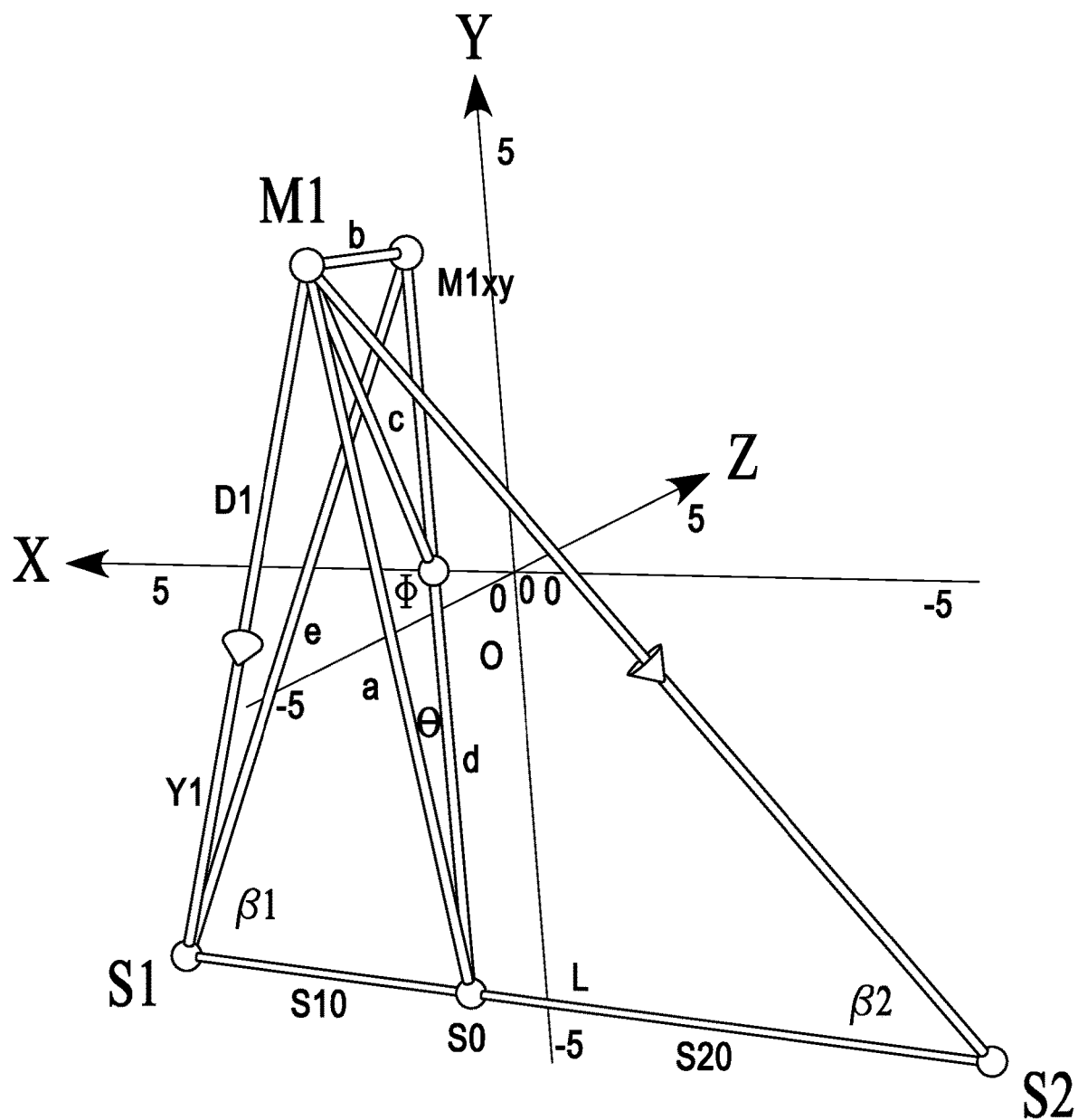
FIG. 11 illustrates a kinematic model for joint angle measurement.

FIG. 11 illustrates a kinematic model for joint angle measurement. In FIG. 11, S1 represents the position of 3D magnetic sensor 111, S2 represents the position of 3D magnetic sensor 112 and M1 represents the position of magnet 121. Positions S1 and S2 are in line with the joint axes. The distance between positions S1 and S2 is known based on the fixed distance between 3D magnetic sensor 111 and 3D magnetic sensor 112 on carrier board 800 or joint pad 27. As is illustrated by FIG. 8, the magnetic field vector H from magnet 121 to 3D magnetic sensor 111 and position of 3D magnetic sensor 112 can be represented as Equation 1 below $$c^2 = a^2 + d^2 - 2 \times a \times d \times \cos\theta \qquad \text{Equation 1}$$

In Equation 1, a, c and d are spatial distances, as shown in FIG. 11, and where $\theta$ is the spatial angle between a and d. In Equation 1 c is the magnet rotation radii. d is the distance from the global origin to the line between 3D magnetic sensor 111 (S1) and 3D magnetic sensor 112 (S2).

Also, for Equation 1, a can be calculated as set out in the Equation below $$a = \frac{L \times B_{x1} \times \sqrt[2]{B_{y2}^2 + B_{z2}^2}}{B_{x2} \times \sqrt[2]{B_{y1}^2 + B_{z1}^2} + B_{x1} \times \sqrt[2]{B_{y2}^2 + B_{z2}^2}} \times \frac{\sqrt[2]{B_{y1}^2 + B_{z1}^2}}{B_{x1}}$$

$$\cos\theta = \frac{B_{y1}}{\sqrt[2]{B_{y1}^2 + B_{z1}^2}}$$

In the equation above, L is the distance between 3D magnetic sensor 111 and 3D magnetic sensor 112. Bx1, By1, Bz1 are readings from 3D magnetic sensor 111 (S1). Bx2, By2, Bz2 are readings from 3D magnetic sensor 112 (S2). a and $\theta$ are known values.

In another sampling point, M1 is rotated around the X axis to another position, as shown in Equation 2 below:

$$c^2 = a'^2 + d^2 - 2 \times a' \times d \times \cos\theta' \qquad \text{Equation 2}$$

In Equation 2, a', c and d are spatial distance and $\theta'$ is the spatial angle between a' and d. Magnet rotation radii c and distance d do not change in joint rotation.

By solving Equation 1 and Equation 2, magnet rotation radii c and distance d can be derived.

Joint moving angle $\phi$ is understood to be:

$$\phi = \cos^{-1} \frac{c^2 + d^2 - a^2}{2 \times c \times d}$$

For a general placement of joint movement monitoring device 911, 3D magnetic sensor 111 and 3D magnetic sensor 112, local measuring coordinate may not be in line with the global coordinate. The sensor readings must be modified with the following transfer function before applying the above kinematic model:

$$\begin{bmatrix} B_{x1}^T \\ B_{y1}^T \\ B_{z1}^T \end{bmatrix} = \begin{bmatrix} B_{x1} \\ B_{y1} \\ B_{z1} \end{bmatrix} \times \begin{bmatrix} \cos\sigma & \sin\sigma & 0 \\ -\sin\sigma & \cos\sigma & 0 \\ 0 & 0 & 1 \end{bmatrix} \times \begin{bmatrix} \cos\rho & 0 & \sin\rho \\ 0 & 1 & 0 \\ -\sin\rho & 0 & \cos\rho \end{bmatrix}$$

In the equation above, angle c is the Z axis rotation angle of 3D magnetic sensor used measuring coordinates for lining up with the joint moving coordinate and angle $\rho$ is the Y axis rotation angle of the 3D magnetic sensor measuring coordinate for lining up with the joint moving coordinate.

Figure 16:
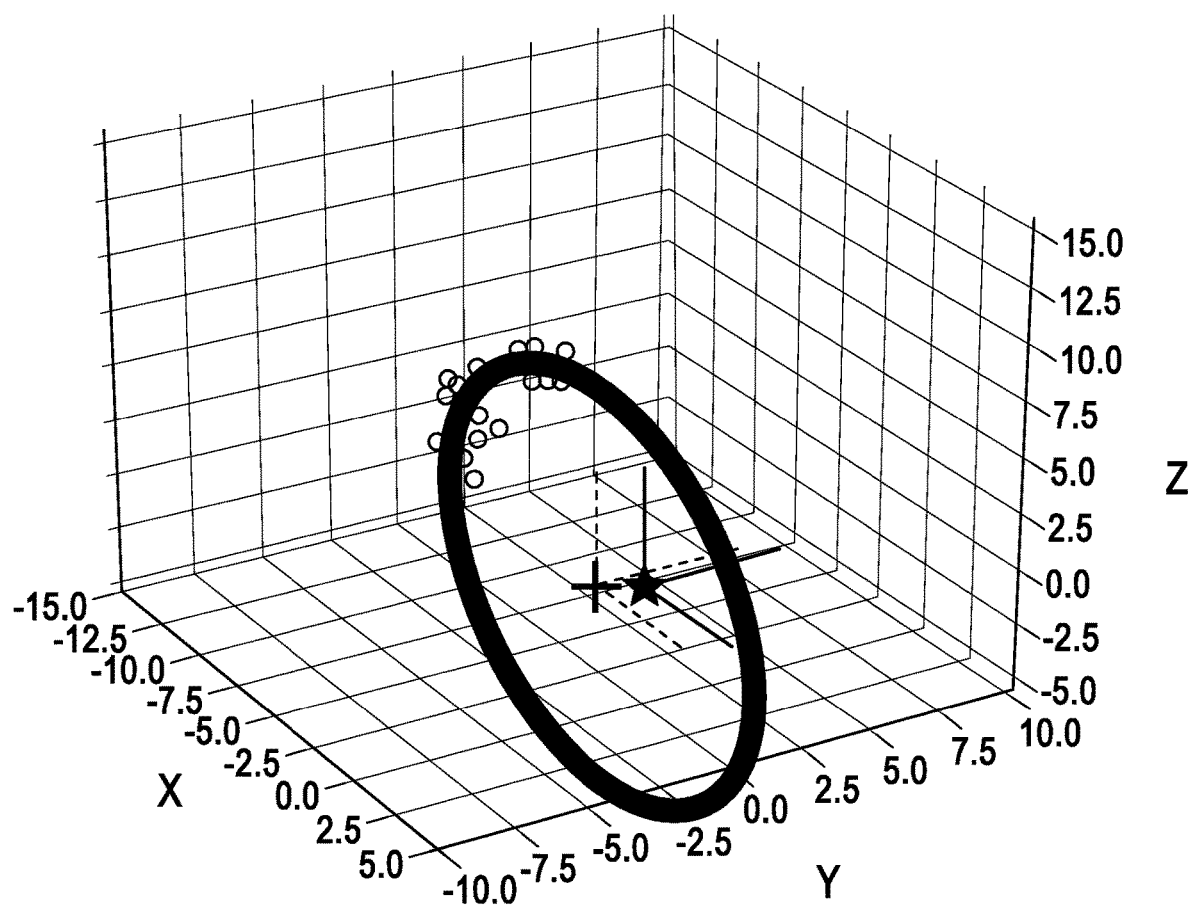
FIG. 16 shows a plot where the joint angle tracking result in squat is illustrated.
Figure 17:
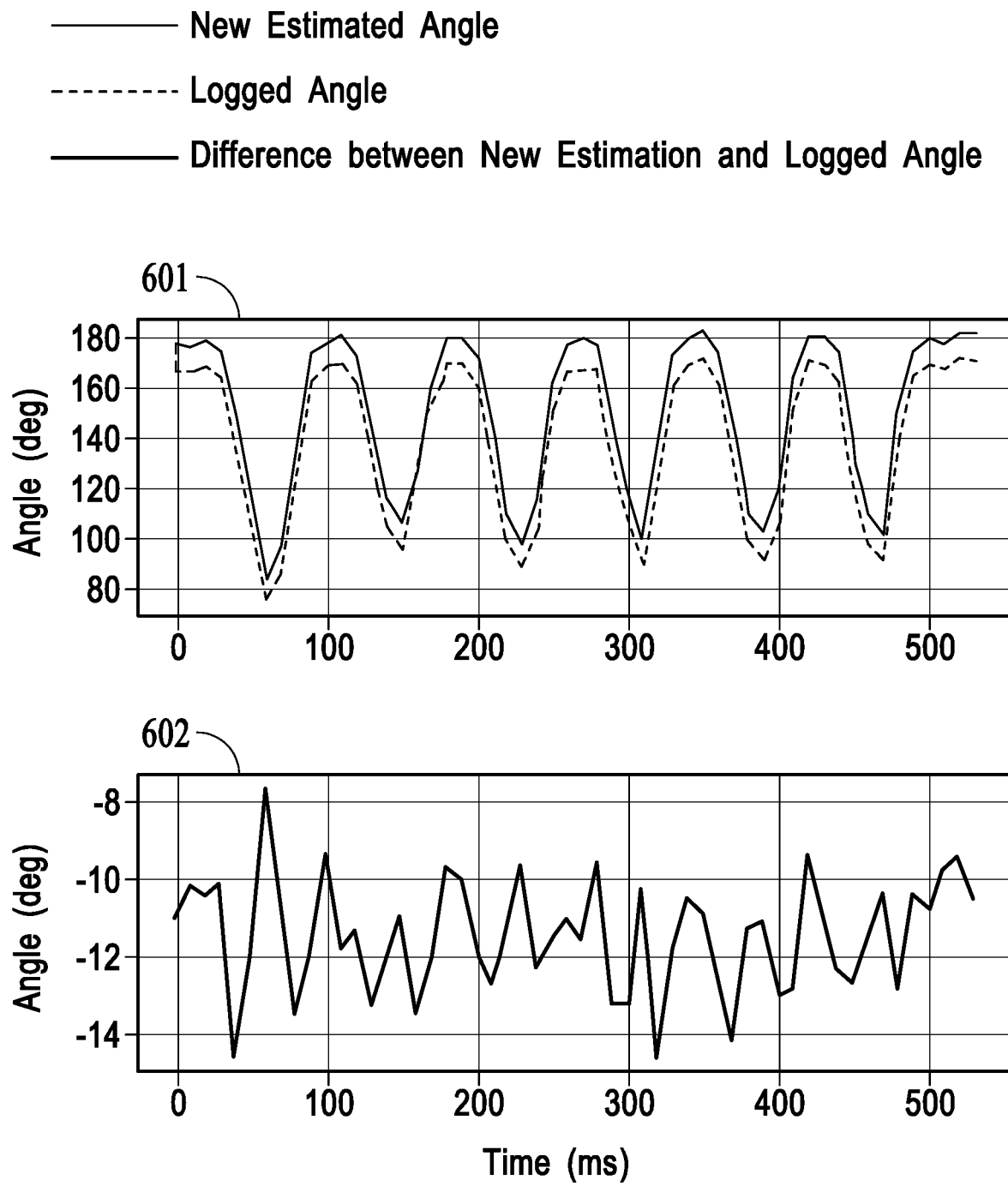
FIG. 17 shows graphs that illustrate the difference between a new estimation and a logged angle.

A third measuring point is needed to calculate angle $\sigma$ and angle $\rho$ using a least square method with Machine learning (ML) and artificial intelligence (AI), accounting for magnet 121 always moving in the same plane. This is illustrated by the 3D plot shown in FIG. 16 where the joint angle tracking result in squat is shown. The 3D plot is calculated using least square and machine learning. In FIG. 17, graph 601 and graph 602 illustrate the difference between the new estimation and the logged angle.

For example, the kinematic model illustrated in FIG. 11 may be used for sensor workspace mapping and magnetic field distortion detection. Magnetic localization systems are susceptible to error induced by magnetic distortions within the magnetic field caused by, for example, extraneous ferrous or metallic objects intruding into the magnetic field. With the above kinematic model, the sensor workspace is defined, and the magnet trajectory is predictable. Any sensor reading outside the workspace will be considered error. Trajectory planning with look-ahead algorithm may be used for field mitigation of magnetic field distortion error in 3D domain.

For example, the look-ahead algorithm can be implemented using the following steps:

Step one, determine the current location of the magnet;
Step two, find the path point closest to the magnet;
Step three, find the goal point;
Step four transform the goal point to magnet coordinates;
Step five, calculate the curvature and configure the trajectory planning tool to the calculated curvature;
Step six, update the magnet's location;

Repeat steps two through six with the updated magnet's location. The path tracking is aborted when the goal is placed out of the desired path.

Figure 12:
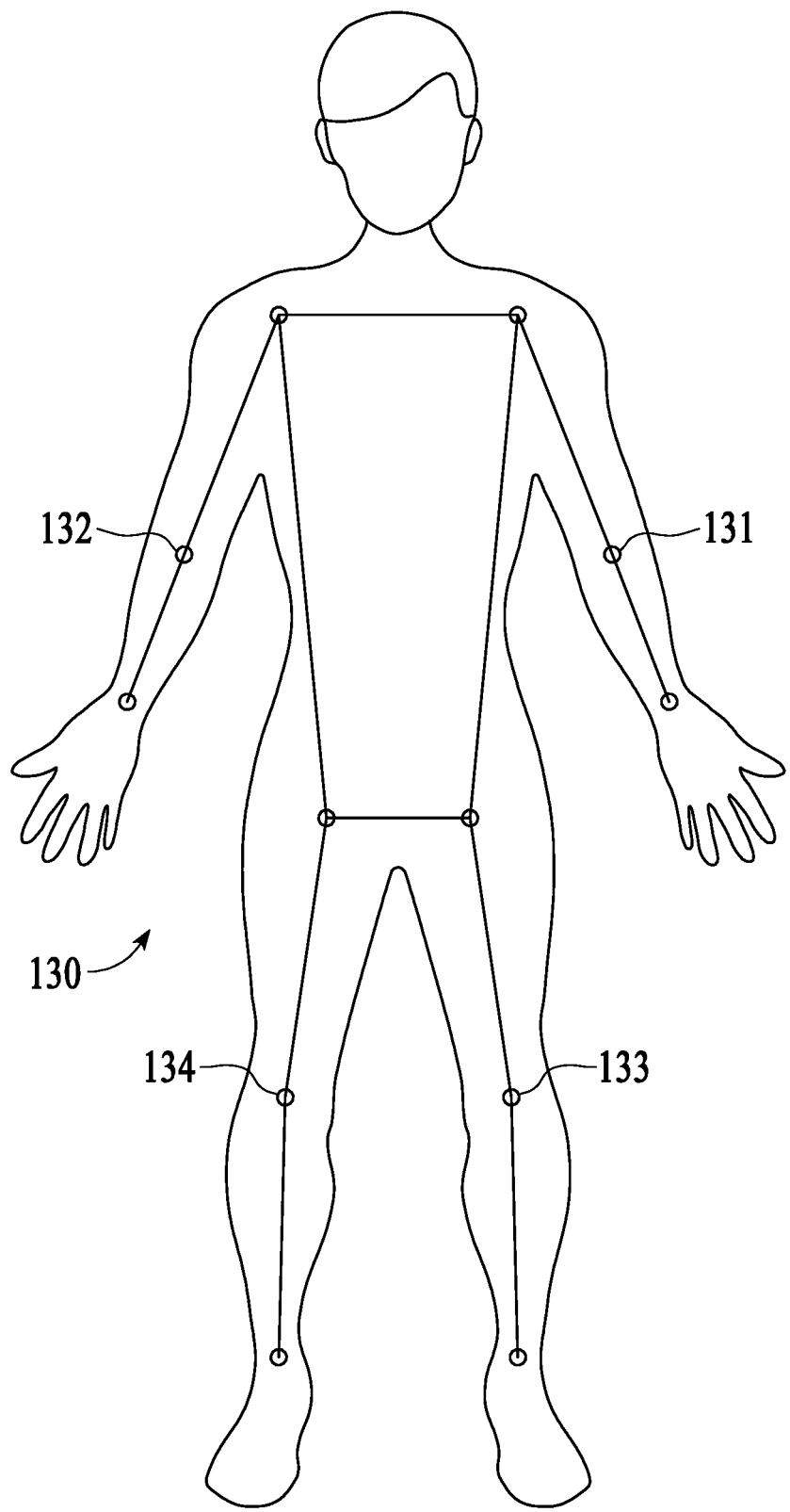
FIG. 12 conceptually illustrates a kinematic model for full body skeletal tracking.

FIG. 12 conceptually illustrates a kinematic model 130 for full body skeletal tracking. As shown, a multiple joint movement monitoring device framework is designed to be linked with the kinematic model. For example, four joint movement monitoring devices, each with two magnetic sensors and one IMU, are fixed to the user's left elbow 131, right elbow 132, left knee 133 and right knee 134. To identify the three different kinds of rotation (flexion-extension, abduction adduction, pronation-supination), each joint movement monitoring device is fixed according to the scheme depicted in FIG. 12 with each joint movement monitoring device fixed on the back of each limb. Each local 3D magnetic sensor axis y is aligned with the associated bone, oriented toward the ground while in a standing pose. The z-axis is pointing toward the interior of this bone. As a consequence, the local rotations along the axes (x, y, z) describe the pronation-supination, the abduction-adduction and the flexion-extension of each limb relative to their associated joint respectively. The IMU adjacent to the two magnetic sensors is oriented the same as the 3D magnetic sensors. The IMU on the four joint movement monitoring devices provides a global coordinate system referenced by gravity for 3D magnetic sensors. For the IMU on the other side, the IMU's integration drifting error can be corrected by the 3D magnetic sensors reading by sensor fusion.

For example, an algorithm that employs a quaternion representation of orientation and is not subject to the problematic singularities associated with Euler angles may be used for effective performance at low computational expense.

FIG. 13 illustrates a block diagram of joint movement monitoring device 911, including a carrier board 800 mounted within joint pad 27 shown in FIG. 6. As shown, carrier board 800 includes a controller 300, 3D magnetic sensor 111, 3D magnetic sensor 112, an RF transmitter 400, an antenna 700, a power supply 500, such as a battery, IMU 191 and biometric sensor 181 connected as shown. For example, controller 300 stores and executes signal processing algorithms and a transmission data protocol. The signal processing algorithms process signals from 3D magnetic sensor 111 and 3D magnetic sensor 112. The processed signals are used to detect magnet 121 rotation angle related to 3D magnetic sensor 111 and 3D magnetic sensor 112. This allows detection and monitoring of joint position and motion of knee joint 23.

For example, IMU 191 is a 6-axis Motion Processing Unit with integrated 3-axis gyroscope, 3-axis accelerometer. 3D magnetic sensor 111 and 3D magnetic sensor 112 are configured to detect magnetic field changes within its detection region as produced by magnet 121 and any other magnets that are moving. As discussed above, other magnets may be added, for example, such as magnet 122 shown in FIG. 5 within its detection region as shown in FIG. 5. As shown in FIG. 6, carrier board 800 and magnet 121 are coupled to joint movement monitoring device 911 implemented as a joint pad 27 having a primary section 24 and an opposing section 25. In such embodiments, carrier board 800 may be coupled to the front, the side or the back of the joint in primary section 24 and magnet 121 may be coupled to the opposing section 25.

Figure 14:
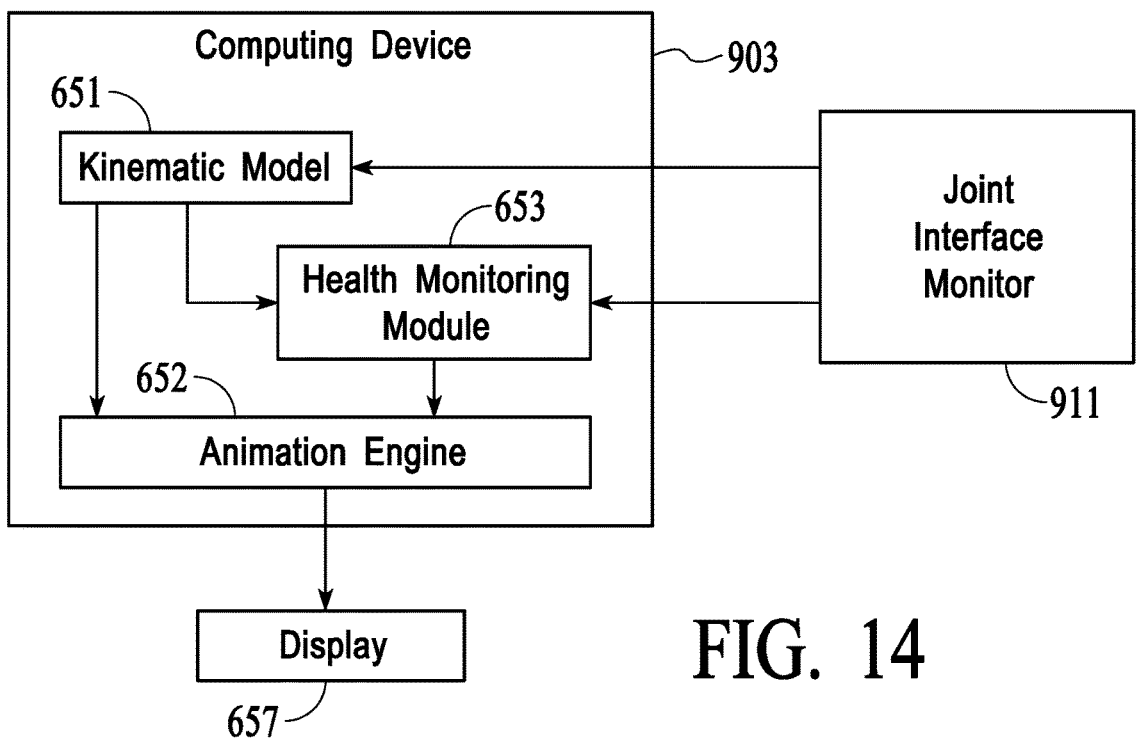
FIG. 14 schematically illustrates a joint movement monitoring system for health monitoring and skeletal tracking.

FIG. 14 schematically illustrates a joint movement monitoring system for health monitoring and skeletal tracking. Joint movement monitoring device 911 provides joint moving data and health indicators (muscle strength, pulse rate etc.) detected/processed from the joint movement monitoring device's various sensors, to a portable computing device 903. For example, portable computing device 903 utilizes a kinematic model 651 to identify dynamic movements of the joint, such as motion and/or changes in the pose of the joint. The derived skeletal joint movement is supplied to an input of an animated engine. For example, the animated skeletal/character model can be monitored and tracked in real-time on a display 657, either locally or remotely.

For example, the skeletal joint movement may also be supplied as input to a health monitoring module 653, and may be combined with other health indicators, such as muscle strength, pulse rate and so on, to derive useful health information, as well as to monitor warning signs of ill health. The result can be monitored and tracked in real-time on a display 657 along with the animation.

Figure 15:
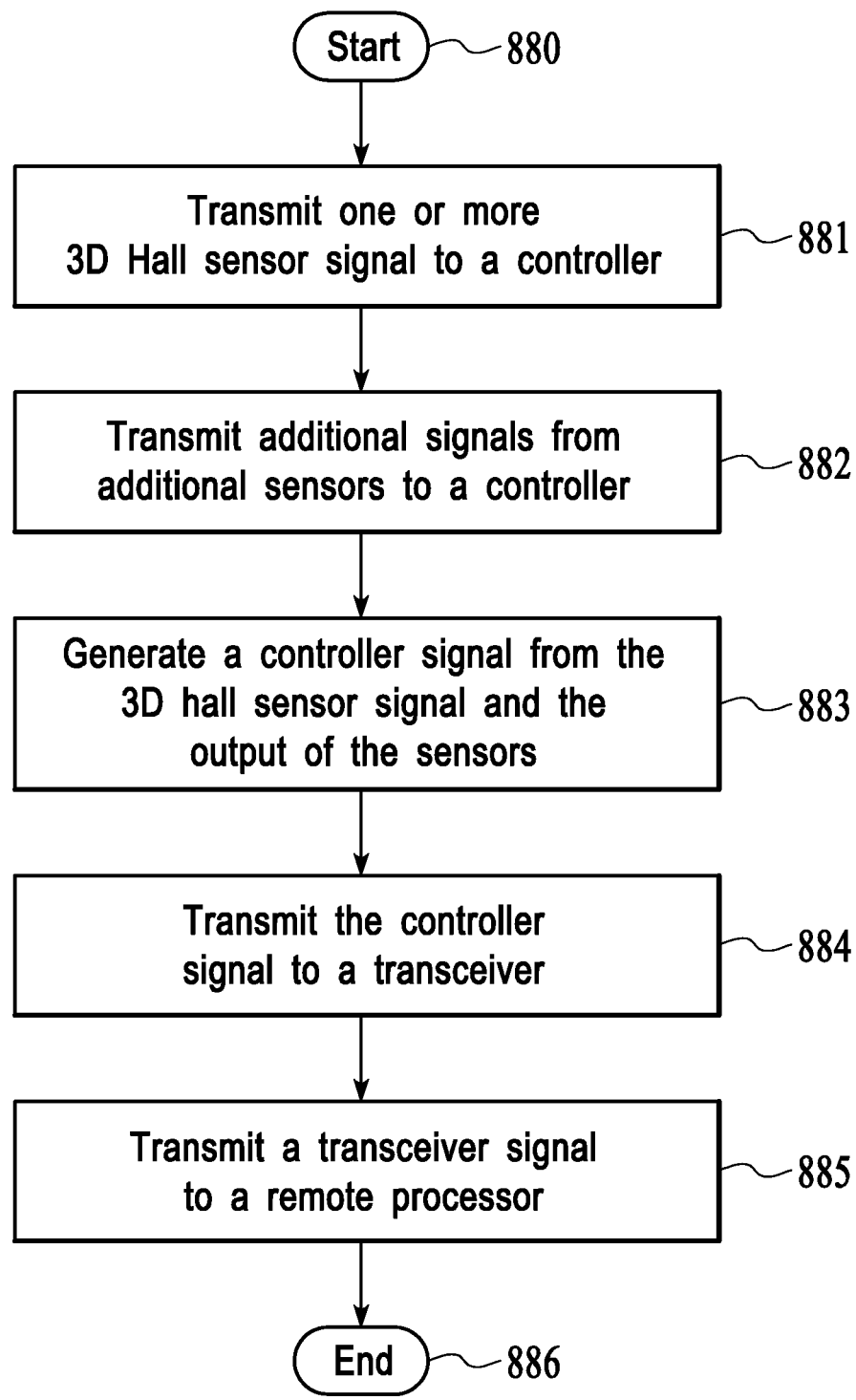
FIG. 15 is a flowchart illustrating a health monitoring and skeletal tracking method.

FIG. 15 is a flowchart illustrating health monitoring and skeletal tracking within a joint movement monitoring system. For illustrative purposes, health monitoring and skeletal tracking is discussed with reference to joint movement monitoring device 911 as shown in FIG. 1 as configured in FIG. 6. For example, in a block 880, health monitoring and skeletal tracking starts. In a block 881, one or more 3D magnetic sensor signals are transmitted to a controller. For the example of joint movement monitoring device 911 as shown in FIG. 1 and as configured in FIG. 6, this can include transmitting, from 3D magnetic sensor 111 and/or 3D magnetic sensor 112, an x, y, z coordinate position signals for three-dimensional magnetic movements to controller 300.

In block 882, additional signals are transmitted from additional sensors to a controller. For the example of joint movement monitoring device 911 as shown in FIG. 1 and as configured in FIG. 6, this can include transmitting output from a sensor, such as a MEMS sensor 211 and/or a biometric sensor 181, to controller 300. For example, in one embodiment biometric sensor 181 may be an EDA sensor. Alternatively, block 882 can be omitted so that block 883 directly follows block 881.

In block 883 a controller signal is generated from the 3D magnetic sensor signal and the output of other sensors. For the example of joint movement monitoring device 911 as shown in FIG. 1 and as configured in FIG. 6, this can include generating a controller signal from the x, y, z coordinate magnet position signal and the output of MEMS sensor 211 and/or biometric 181. Block 883 may be performed by logic stored within controller 300.

For example, optionally, in a block 854 the controller signal is transmitted to a receiver. For the example of joint movement monitoring device 911 as shown in FIG. 1 and as configured in FIG. 6, this can be performed using transmitter 400 connected to controller 300.

For example, optionally, in a block 855 a transceiver signal is transmitted to a remote processor. For the example of joint movement monitoring device 911 as shown in FIG. 1 and as configured in FIG. 6, this can include transmitting a transmitter signal to a remote processor, such as portable device 903 shown in FIG. 1, via antenna 700. For example, block 885 may be performed by logic stored within controller 300. For example, controller 300 may decide not to transmit position signal and/or other sensor output if no significant change of the data to reduce battery consumption. For example, controller 300 will not transmit x, y, z coordinate magnet position data if a user is standing still.

The foregoing discussion discloses and describes merely exemplary methods and embodiments. As will be understood by those familiar with the art, the disclosed subject matter may be embodied in other specific forms without departing from the spirit or characteristics thereof. Accordingly, the present disclosure is intended to be illustrative, but not limiting, of the scope of the invention, which is set forth in the following claims.

What is claimed is:

1. A joint movement monitoring device, comprising:
   a joint pad that fits over a joint, the joint pad having a primary section placed over a first side of the joint and having an opposing section placed over a second side of the joint;
   a magnet incorporated into the opposing section of the joint pad, the magnet generating a magnetic field;
   a plurality of three-dimensional (3D) magnetic sensors incorporated into the primary section of the joint pad, the 3D magnetic sensors being separated by a known distance, each of the 3D magnetic sensors detecting the magnetic field generated by the magnet incorporated into the opposing section of the joint pad; and
   a controller that processes signals from the 3D magnetic sensors, the signals being based on detected strength and direction of the magnetic field generated by the magnet incorporated into the opposing section of the joint pad, wherein signals processed by the controller are used to detect magnet rotation angles and distances related to 3D magnetic sensors within the plurality of 3D magnetic sensors, the detected magnet rotation angles and distances being used to monitor joint position and motion.

2. A joint movement monitoring device as in claim 1 wherein the plurality of 3D magnetic sensors and the controller are mounted on a carrier board attached to the primary section of the joint pad.

3. A joint movement monitoring device as in claim 1, additionally comprising,
   an additional magnet incorporated into the primary section of the joint pad.

4. A joint movement monitoring device as in claim 1, additionally comprising, one or more microelectromechanical systems (MEMS) sensors incorporated into the primary section of the joint pad.

5. A joint movement monitoring device as in claim 1, additionally comprising, one or more inertial measurement unit (IMU) sensor incorporated the joint pad.

6. A joint movement monitoring device as in claim 1, additionally comprising, an electrodermal activity (EDA) sensor incorporated into the joint pad.

7. A joint movement monitoring device as in claim 1, additionally comprising, a photoplethysmography (PPG) sensor incorporated into the primary section of the joint pad.

8. A joint movement monitoring device as in claim 1, additionally comprising, an acoustic emission (AE) sensor incorporated into the primary section of the joint pad.

9. A joint movement monitoring device as in claim 1, wherein the joint pad is sized to fit over a knee joint.

10. A joint movement monitoring device as in claim 1, wherein the joint pad is sized to fit over an elbow joint.

11. A joint movement monitoring device as in claim 1, wherein the controller communicates with a portable device configured to execute a health monitoring application for fusing data and generating a skeletal model that can be monitored and tracked in real time on a display of the portable device.

12. A joint movement monitoring system, comprising:
   a first joint movement monitoring device, including:
      a joint pad that fits over a first joint, the joint pad having a primary section placed over a first side of the first joint and having an opposing section placed over a second side of the first joint,
      a magnet incorporated into the opposing section of the joint pad, the magnet generating a magnetic field,
      a plurality of three-dimensional (3D) magnetic sensors incorporated into the primary section of the joint pad, the 3D magnetic sensors within the plurality of 3D magnetic sensors being separated by a known distance, each of the 3D magnetic sensors detecting the magnetic field generated by the magnet incorporated into the opposing section of the joint pad, and
      a controller that obtains signals from the plurality of 3D magnetic sensors, the signals being based on detected strength and direction of the magnetic field generated by the magnet incorporated into the opposing section of the joint pad, the signals being used to detect magnet rotation angles and distances related to 3D magnetic sensors within the plurality of 3D magnetic sensors, the detected magnet rotation angles and distances being used to monitor joint position and motion; and
   a portable device configured to execute a health monitoring application for fusing data and generating a skeletal model that can be monitored and tracked in real time on a display.

13. A joint movement monitoring system as in 12, wherein the portable device is connected through a network to a cloud-based health monitoring center that monitors biomarkers including fatal signs.

14. A joint movement monitoring system as in 12, additionally comprising:
   three additional joint movement monitoring devices;
   wherein the first joint movement monitoring device and the three additional joint movement monitoring devices are configured to fit on two elbow joints and two knee joints of a single user.

15. A joint movement monitoring system as in 12, additionally comprising:
   an additional joint movement monitoring device;
   wherein the first joint movement monitoring device and the additional joint movement monitoring devices are configured to fit on two knee joints of a single user.

16. A joint movement monitoring system as in 12, additionally comprising:
   an additional joint movement monitoring device;
   wherein the first joint movement monitoring device and the additional joint movement monitoring devices are configured to fit on two elbow joints of a single user.

17. A joint movement monitoring system as in 12, wherein the portable device is connected through a network to a cloud-based health monitoring center that creates a world scene the portable device and other portable devices interact with each other, communicating and sharing information skeletal models.

18. A joint movement monitoring system as in 17, wherein within the world scene, speaking volume is weighed based on distance between persons within the world scene.

19. A joint movement monitoring device, comprising:
a joint pad that fits over a joint, the joint pad having a primary section placed over a first side of the joint and having an opposing section placed over a second side of the joint;
a magnet incorporated into the opposing section of the joint pad, the magnet generating a magnetic field;
a first three-dimensional (3D) magnetic sensor incorporated into the primary section of the joint pad, the first 3D magnetic sensor detecting the magnetic field generated by the magnet incorporated into the opposing section of the joint pad;
a second 3D magnetic sensor incorporated into the primary section of the joint pad, the second 3D magnetic sensor detecting the magnetic field generated by the magnet incorporated into the opposing section of the joint pad, wherein the first 3D magnetic sensor and the second 3D magnetic sensor are separated by a known distance;
a first IMU sensor incorporated into the primary section of the joint pad;
a second IMU incorporated into the opposing section of the joint pad; and
a controller that processes signals from the first IMU sensor, the second IMU sensor, the first 3D magnetic sensor and the second 3D magnetic sensor in order to monitor joint position and motion, wherein signals processed by the controller are used to detect orientations of the first IMU sensor and the second IMU sensor, and wherein signals processed by the signal controller are used to detect magnet rotation angles and distances related to the first 3D magnetic sensor and the second 3D magnetic sensor.

20. A joint movement monitoring device as in claim 19, wherein the controller utilizes the known distance to calculate spatial distances and a rotation radii when monitoring joint position and motion.

* * * * *